United States Patent
Dakternieks et al.

(10) Patent No.: US 6,696,611 B2
(45) Date of Patent: Feb. 24, 2004

(54) CHEMICAL METHODS

(75) Inventors: Dainis Dakternieks, Highton (AU); Carl H. Schiesser, Highton (AU); Tamara Perchyonok, Caulfield (AU)

(73) Assignee: Chirogen Pty. Limited, Highton (AU)

( * ) Notice: Subject to any disclaimer, the term of this patent is extended or adjusted under 35 U.S.C. 154(b) by 0 days.

(21) Appl. No.: 09/917,415

(22) Filed: Jul. 27, 2001

(65) Prior Publication Data

US 2002/0133039 A1 Sep. 19, 2002

Related U.S. Application Data

(60) Provisional application No. 60/221,071, filed on Jul. 27, 2000.

(51) Int. Cl.[7] .............................................. C07C 45/00
(52) U.S. Cl. ........................ 568/316; 560/101; 560/105; 562/553; 562/559; 562/562; 562/563; 562/570; 562/573; 562/575; 562/576; 568/331
(58) Field of Search ................................. 568/316, 331; 560/101, 105; 562/559, 562, 563, 570, 573, 575, 576, 553

(56) References Cited

PUBLICATIONS

Blumenstein, Angewandte Chemie, Ineternational Edition in English, vol. 36(3), pp. 235–236 (1997).*

Nanni, Tetrahedron: Asummetry, vol. 7(8), pp. 2417–2422 (1996).*

English translation of "Enantioselective radical reaction by chiral Lewis acid," *Kagaku* (*Kyoto*), 54:70–71, 1999.

* cited by examiner

*Primary Examiner*—Michael L. Shippen
(74) *Attorney, Agent, or Firm*—Williams, Morgan & Amerson, P.C.

(57) ABSTRACT

The present invention provides a method for enantioselectively reducing a prochiral carbon centered radical having one or more electron donator groups attached directly to the central prochiral carbon atom of the radical, and/or attached to a carbon atom within 1 to 4 atoms of the central prochiral carbon atom, comprising treating said radical with a chiral non-racemic organotin hydride in the presence of a Lewis acid.

10 Claims, No Drawings

CHEMICAL METHODS

The present application claims priority from U.S. provisional application Ser. No. 60/221,071, filed Jul. 27, 2000, the entire contents of which is specifically incorporated herein by reference in its entirety.

BACKGROUND OF THE INVENTION

FIELD OF THE INVENTION

The present invention relates generally to reductive methods useful in chemical synthesis. In particular, the present invention provides enantioselective reductive methods using chiral organostannanes and Lewis acids.

The scientific literature contains numerous reports of free-radical reactions proceeding with distereocontrol (see for example, reviews such as Curran et al., *Stereochemistry of Radical Reactions*, VCH, Weinheim, 1995; Smadja et al., *Synlett.*, 1, 1994; Porter et al., *Acc. Chem. Res.*, 24:296, 1991; and Sibi et al., *Acc. Chem. Res.*, 32:163, 1999). However, there are relatively very few examples of free-radical reactions which proceed with genuine enantiocontrol. The majority of the examples that demonstrate enantioselective outcomes involve the use of chiral auxiliaries and, as a result, are actually further examples of diastereoselectivity in free-radical chemistry.

Of the remaining few reports, the introduction of asymmetry in the substrate has been achieved through the use of chiral Lewis acid mediation (see, for example, Guindon et al., *Tetrahedron Lett.*, 31:2845, 1990; Guindon et al., *J. Am. Chem. Soc.*, 113:9701, 1991; and Renaud et al., *Angew. Chem. Int. Ed.*, 37:2563, 1998), or by a chiral reagent through the use of chiral ligands on the tin atoms in suitably constructed stannanes (Schumann et al., *J. Organomet. Chem.*, 265:145, 1984; Curran et al., *Tetrahedron. Asymmetry*, 7:2417, 1996; Blumstein et al., *Angew. Chem. Int. Ed.*, 36:235, 1997; and Schartzkopfetal., *Eur. J. Chem.*, 177, 1998).

It has now been found that the enantioselectivity of free radical reductions using chiral non-racemic stannanes can be enhanced by the use of an appropriate Lewis Acid.

SUMMARY OF THE INVENTION

Throughout this specification and the claims which follow, unless the context requires otherwise, the word "comprise", and variations such as "comprises" and "comprising," will be understood to imply the inclusion of a stated integer or step or group of integers or steps but not the exclusion of any other integer or step or group of integers or steps.

Improved methods for the enantioselective reduction of prochiral carbon radicals using chiral and achiral Lewis acids in conjunction with chiral non-racemic stannanes have now been developed which result in an enhanced enantioselectivity when compared to the use of the chiral non-racemic stannane alone.

Accordingly, the present invention provides a method for enantioselectively reducing a prochiral carbon centred radical having one or more electron donor groups attached directly to the central prochiral carbon atom of the radical, and/or attached to a carbon atom within 1 to 4 atoms of the central prochiral carbon atom, comprising treating said radical with a chiral non-racemic organotin hydride in the presence of a Lewis acid.

Preferably, the electron donor group is attached directly to the central prochiral carbon atom or to a carbon atom within 1 or 2 atoms of the central prochiral carbon atom.

In a particular embodiment, the invention is directed towards a method of producing optically enhanced α or β-amino acids, by treatment of a prochiral amino acid carbon centred radical with a chiral non-racemic organotin hydride in the presence of a Lewis acid, wherein the central prochiral carbon atom is an α-carbon atom of an α-amino acid.or a β-carbon atom of a β-amino acid.

DETAILED DESCRIPTION OF THE INVENTION

As used herein, the term "prochiral carbon centred radical" is a radical of formula $R^1R_2R_3C.$, wherein each R residue is different and is not hydrogen. Accordingly, the central prochiral carbon atom is the carbon atom to which the R residues are attached. Reduction of the prochiral carbon centred radical with a hydrogen atom donor affords the chiral compound $R_1R_2R_3CH$. The present invention thus relates to the preparation of enantioselectively enhanced chiral compounds.

The prochiral carbon centred radical can be generated from any suitable radical precursor using methods known in the art. Exemplary radical precursors include aryl, e.g., phenyl, selenides; aryl, e.g., phenyl, sulfides; aryl, e.g., phenyl, tellurides; xanthates; thionoformates and Barton esters (see, for example, Giese, *Radicals in Organic Synthesis— Formation of C—C Bonds*, Pergamon Press, Oxford, 1986, the contents of which are incorporated herein by reference). Particularly suitable radical precursors for generating the prochiral carbon centred radicals for use in the invention are tertiary chiral halosubstrates, i.e., $R_1R_2R_3C$-halogen, where $R_1$–$R_3$ are different and not hydrogen and halogen is chlorine, bromine or iodine, preferably bromine.

The prochiral carbon centred radicals which can be reduced by the methods of the invention include radicals which bear one or more electron donor groups directly on the prochiral central carbon atom and/or attached to a carbon atom or to the central prochiral carbon atom, i.e., within 1, 2, 3 or 4 atoms, preferably within 1 or 2 atoms. Suitable electron donor groups include those containing an electron donor atom such as oxygen, nitrogen, and/or sulfur and which will not be affected by the organotin hydride. One example of an electron donor group is a carbonyl group $C(=O)$, present, as, for example, in aldehydes, ketones, carboxy acid, carboxy esters, carboxy amides, anhydrides, lactones, lactams, carbonates, carbamates and thioesters, etc. Other electron donor groups include, thioalkyl groups, amines (unsubstituted or substituted once or twice by, for example, a group selected from alkyl, acyl and aryl), hydroxy groups and ethers (e.g., alkyl and aryl). A preferred electron donor is a carbonyl group. Preferably the carbonyl group is adjacent to, i.e.,—to the chiral carbon to be reduced. Expressed in another way, the prochiral carbon centred radical has at least one electron donor atom within 5 atoms (i.e., 1, 2, 3, 4, or 5) of the central prochiral carbon atom. It will be recognized that some electron donor groups may contain one or more electron donating atoms, e.g., carboxy acid, carboxy ester, thioester, carboxy amide. A prochiral carbon centred radical may also contain more than one electron donating group attached to the central prochiral atom.

Exemplary prochiral carbon centred radicals include those of the formula $R_1R_2R_3C.$, wherein $R_1$–$R_3$ are different (and not hydrogen) and are independently selected from alkyl, alkenyl, alkynyl, aryl, heterocyclyl, acyl, amino, substituted amino, carboxy, anhydride, carboxy ester, carboxy amide, lactone, lactam, thioester, formyl, optionally protected hydroxy, thioalkyl, alkoxy, alkenyloxy, alkynyloxy, aryloxy, heterocyclyloxy; or alternatively, any two of $R_1$–$R_3$ can together, with the central prochiral carbon atom, form a mono- or poly-cyclic group or fused polycyclic group including as cycloalkyl, cycloalkenyl, cycloalkynyl, a lactone, a lactam, cyclic anhydride, or heterocyclyl and bi-, tri- and tetracyclic fused combinations thereerof. At least one of $R_1$–$R_3$, or a cyclic group formed by any two of $R_1$–$R_3$, contains an electron donator atom within 1 to 5 atoms of the prochiral central carbon atom to be reduced. It will be understood that a radical precursor may contain more than one prochiral radical precursor sites and that reduction may therefore occur at one or more of these sites.

In one preferred embodiment, at least one of $R_1$–$R_3$ is an optionally substituted aryl or heteroaryl group. In another preferred embodiment at least one of $R_1$–$R_3$ is an optionally substituted alkyl, alkenyl, or alkynyl group. In another embodiment, at least one of $R_1$–$R_3$ is a ketone, aldehyde, carboxy acid, carboxy ester, carboxy amide, anhydride, lactone, lactam or thioester, or two of $R_1$–$R_3$ together with the central prochiral carbon atom form a cyclic anhydride, lactam or lactone.

Preferred "ketones" have the formula —C(O)—R wherein R can be any residue, having a carbon atom covalently bonded to the carbonyl group, such as alkyl, alkenyl, alkynyl and aryl. An R group may have one or more carbon atoms optionally replaced with one or more heteroatoms to form, for example, heterocyclyl.

Preferred "carboxy esters" have the formula —CO₂R wherein R can be any residue, having a carbon atom covalently bonded to the non-carbonyl oxygen atom, for example, alkyl, alkenyl, alkynyl or aryl. An R group may have one or more carbon atoms optionally replaced with one or more heteroatoms, such that R is, for example, heterocyclyl.

Preferred "carboxy amides" have the formula CO₂NRR' wherein R and R' are independently selected from hydrogen and any residue having a carbon atom covalently bonded to the nitrogen atom such as alkyl, alkenyl, alkynyl or aryl. An R or R' group may have one or more carbon atoms optionally replaced with one or more heteroatoms to form, for example, heterocyclyl.

Preferred "thioesters" have the formula —C(O)SR wherein R can be any residue having a carbon atom covalently bonded to the sulfur atom, such as alkyl, alkenyl, alkynyl or aryl. An R group may have one or more carbon atoms optionally replaced with one or more heteroatoms to form, for example, heterocyclyl.

Preferred anhydrides contain the moiety —C(O)—OC(O)— and may be cyclic or acyclic. Preferred acyclic anhydrides contain the moiety —C(O)—O—C(O)—R wherein R can be any residue, such as alkyl, alkenyl, alkynyl or aryl. An R group may have one or more carbon atoms optionally replaced with one or more heteroatoms to form, for example, heterocyclyl. Preferred cyclic anhydrides contain the moiety —C(O)—O—C(O)—(CH₂)ₙ— wherein n is 1, e.g., 1, 2, 3, 4, 5 or 6.

Lactones are cyclic residues containing the moiety —C(O)O—. Preferred lactones have the formula —C(O)O—R— wherein —R— can be any residue, having a carbon atom covalently bonded to the non-carbonyl oxygen atom, e.g., alkylene, alkenylene, alkynylene. An R group may have one or more carbon atoms optionally replaced by one or more heteroatoms. Preferred lactones contain the moiety —C(O)—O—(CH₂)ₙ— wherein n is 2, e.g., 2, 3, 4, 5 or 6.

Lactams are cyclic residues containing the moiety —C(O)—N(R')—R— wherein R' can be hydrogen or any hydrocarbon residue such as alkyl, acyl, aryl or alkenyl. —R— can be any hydrocarbon residue having a carbon atom covalently bonded to the nitrogen atom such as alkylene, alkenylene or alkynylene. An R' or R group may have one or more carbon atoms optionally replaced by one or more heteroatoms. Preferred lactams contain the moiety —C(O)—N(R')—(CH₂)ₙ— wherein n is 2, eg., 2, 3, 4, 5 or 6.

As used herein, the term "alky", denotes straight chain, branched or cyclic hydrocarbon residues, preferably $C_{1-20}$ alkyl, e.g., $C_{1-10}$ or $C_{1-6}$. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2-, or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like. Where an alkyl group is referred to generally as "propyl", "butyl" etc, it will be understood that this can refer to any of straight, branched and cyclic isomers. An alkyl group may be optionally substituted by one or more optional substituents as herein defined. Accordingly, "alkyl" as used herein is taken to refer to optionally substituted alkyl. Cyclic alkyl may refer to monocyclic alkyl or, polycyclic fused or non-fused carbocyclic groups.

The term "alkenyl" as used herein denotes groups formed from straight chain, branched or cyclic hydrocarbon residues containing at least one carbon to carbon double bond including ethylenically mono-, di- or poly-unsaturated alkyl or cycloalkyl groups as previously defined, preferably $C_{1-20}$ alkenyl (e.g., $C_{1-10}$ or $C_{1-6}$). Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. An alkenyl group may be optionally substituted by one or more optional substitutents as herein defined. Accordingly, "alkenyl" as used herein is taken to refer to optionally substituted alkenyl. Cyclic alkenyl may refer to monocyclic alkenyl or, polycyclic fused or non-fused alkenyl carbocyclic groups.

As used herein the term "alkynyl" denotes groups formed from straight chain, branched or cyclic hydrocarbon residues containing at least one carbon-carbon triple bond including ethynically mono-, di- or poly-unsaturated alkyl or cycloalkyl groups as previously defined. Unless the number of carbon atoms is specified the term preferably refers to $C_{1-20}$ alkynyl. Examples include ethynyl, 1-propynyl, 2-propynyl, and butynyl isomers, and pentynyl isomers. An alkynyl group may be optionally substituted by one or more optional substitutents as herein defined. Accordingly, "alkynyl" as used herein is taken to refer to optionally substituted alkynyl. Cyclic alkynyl may refer to monocyclic alkynyl or, polycyclic fused or non-fused alkynyl carbocyclic groups.

The terms "alkoxy," "alkenoxy," "alkenoxy," "aryloxy" and "heterocyclyloxy," respectively, denote alkyl, alkenyl, alkynyl, aril and heterocylclyl groups as hereinbefore defined when linked by oxygen.

The term "halogen" denotes chlorine, bromine or iodine.

The term "aryl" denotes single, polynuclear, conjugated and fused residues of aromatic hydrocarbon ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Aryl may be optionally substituted as herein defined and thus "aryl" as used herein is taken to refer to optionally substituted aryl.

The term "heterocyclic" denotes mono- or polycarbocyclic groups, which may be fused or conjugated, aromatic (heteroaryl) or non-aromatic, wherein at least one carbon atom is replaced by a heteroatom, preferably selected from nitrogen, sulphur and oxygen. Suitable heterocyclic groups include N-containing heterocyclic groups, such as: (1) unsaturated 3 to 6 membered heteromonocyclic groups containing 1 to 4 nitrogen atoms, for example, pyrrolyl, pyrrolinyl, imidazolyl, imidazolinyl, pyrazolyl, pyridyl, pyrimidinyl, pyrazinyl, pyridazinyl, triazolyl or tetrazolyl; (2) saturated 3 to 6-membered heteromonocyclic groups containing 1 to 4 nitrogen atoms, such as, pyrrolidinyl, imidazolidinyl, piperidyl, pyrazolidinyl or piperazinyl; (3) condensed saturated or unsaturated heterocyclic groups containing 1 to 5 nitrogen atoms, such as, indolyl, isoindolyl, indolinyl, isoindolinyl, indolizinyl, isoindolizinyl, benzimidazolyl, quinolyl, isoquinolyl, indazolyl, benzotriazolyl, purinyl, quinazolinyl, quinoxalinyl, phenanthradinyl, phenathrolinyl, phthalazinyl, naphthyridinyl, cinnolinyl, pteridinyl, perimidinyl or tetrazolopyridazinyl; (4) saturated 3 to 6-membered heteromonocyclic groups containing 1 to 3 oxygen atoms, such as tetrahydrofuranyl, tetrahydropyranyl, tetrahydrodioxinyl; (5) unsaturated 3 to 6-membered hetermonocyclic group containing an oxygen atom, such as, pyranyl, dioxinyl or furyl; (6) condensed saturated or unsaturated heterocyclic groups containing 1 to 3 oxygen atoms, such as benzofuranyl, chromenyl or xanthenyl; (7) unsaturated 3 to 6-membered heteromonocyclic group containing 1 to 2 sulphur atoms, such as, thienyl or dithiolyl; (8) unsaturated 3 to 6-membered heteromonocyclic group containing 1 to 2 oxygen atoms and 1 to 3 nitrogen atoms, such as, oxazolyl, oxazolinyl, isoxazolyl, furazanyl or oxadiazolyl; (9) saturated 3 to 6-membered heteromonocyclic group containing 1 to 2 oxygen atoms and 1 to 3 nitrogen atoms, such as, morpholinyl; (10) unsaturated condensed heterocyclic group containing 1 to 2 oxygen atoms and 1 to 3 nitrogen atoms, such as, benzoxazolyl or benzoxadiazolyl; (11) unsaturated 3 to 6-membered heteromonocyclic group containing 1 to 2 sulphur atoms and 1 to 3 nitrogen atoms, such as, thiazolyl, thiazolinyl or thiadiazoyl; (12) saturated 3 to 6-membered heteromonocyclic group containing 1 to 2 sulphur atoms and 1 to 3 nitrogen atoms, such as, thiazolidinyl, thiomorphinyl; and (13) unsaturated condensed heterocyclic group containing 1 to 2 sulphur atoms and 1 to 3 nitrogen atoms, such as, benzothiazolyl or benzothiadiazolyl. A heterocyclic group may be optionally substituted by an optional substituent as described herein.

The term "acyl" denotes a group containing the moiety C=O (and not being a carboxylic acid, ester or amide or thioester). Preferred acyl includes C(O)—R, wherein R is hydrogen or an alkyl, alkenyl, alkynyl, aryl or heterocyclyl, residue, preferably a $C_{1-20}$ residue. Examples of acyl include formyl; straight chain or branched alkanoyl such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g., phenylacetyl, phenylpropanoyl, phenylbutanoyl, phenylisobutylyl, phenylpentanoyl and phenylhexanoyl) and naphthylalkanoyl (e.g., naphthylacetyl, naphthylpropanoyl and naphthylbutanoyl); aralkenoyl such as phenylalkenoyl (e.g., phenylpropenoyl, phenylbutenoyl, phenylmethacryloyl, phenylpentenoyl and phenylhexenoyl and naphthylalkenoyl, e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. Acyl also refers to optionally substituted acyl.

The term "acyloxy" refers to acyl, as herein before defined, when linked by oxygen.

In this specification "optionally substituted" is taken to mean that a group may or may not be further substituted or fused (so as to form a condensed polycyclic group) with one or more groups selected from alkyl, alkenyl, alkynyl, aryl, hydroxy, alkoxy, alkenyloxy, aryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, acyl, acylamino, diacylamino, acyloxy, alkylsulphonyloxy, arylsulphenyloxy, heterocyclyl, heterocycloxy, heterocyclamino, carboalkoxy, carboaryloxy, alkylthio, arylthio, acylthio, cyano, nitro, sulfate and phosphate groups.

Preferred optional substitutents include alkyl, (e.g., $C_{1-6}$ alkyl such as methyl, ethyl, propyl, butyl, cyclopropyl, cyclobutyl, cyclopentyl or cyclohexyl), hydroxyalkyl (e.g., hydroxymethyl, hydroxyethyl, hydroxypropyl), alkoxyalkyl (e.g, methoxymethyl, methoxyethyl, methoxypropyl, ethoxymethyl, ethoxyethyl, ethoxypropyl, etc.), alkoxy (e.g., $C_{1-6}$ alkoxy such as methoxy, ethoxy, propoxy, butoxy, cyclopropoxy, cyclobutoxy), halo, trifluoromethyl, trichloromethyl, tribromomethyl. hydroxy, phenyl (which itself may be further substituted), benzyl (wherein benzyl itself may be further substituted), phenoxy (wherein phenyl itself may be further substituted), benzyloxy (wherein benzyl itself may be further substituted), amino, alkylamino (e.g., $C_{1-6}$alkyl, such as methylamino, ethylamino, propylamino, etc.), dialkylamino (e.g., $C_{1-6}$ alkyl, such as dimethylamino, diethylamino, dipropylamino), acylamino (e.g., NHC(O)CH$_3$), phenylamino (wherein phenyl itself may be further substituted), nitro, formyl, —C(O)—alkyl (e.g., C1-6 alkyl, such as acetyl), O—C(O)—alkyl (e.g., $C_{1-6}$ alkyl, such as acetyloxy), benzoyl (wherein the phenyl group of the benzoyl may itself be further substituted), carbonyl, (i.e., replacement of CH$_2$ with C=O) CO$_2$H, CO$_2$alkyl (e.g., $C_{1-6}$ alkyl such as methyl ester, ethyl ester, propyl ester, butyl ester), CO$_2$ phenyl (wherein phenyl itself may be further substituted), CONH$_2$, CONHphenyl (wherein phenyl itself may be further substituted), CONHbenzyl (wherein benzyl itself may be further substituted), CONHalkyl (e.g., $C_{1-6}$ alkyl such as methyl ester, ethyl ester, propyl ester, butyl amide), CONHdialkyl (e.g., $C_{1-6}$ alkyl).

As used herein, "heteroatom" refers to any atom other than a carbon atom which may be a ring-member of a cyclic organic compound. Examples of suitable heteroatoms include nitrogen, oxygen, sulfur, phosphorous, boron, silicon, arsenic, sellenium and telluruim.

Exemplary chiral non-racemic organotin hydrides have the formula L$_1$L$_2$L$_3$SnH wherein L$_1$–L$_3$ are ligands, which may be the same or different, and wherein at least one of L$_1$–L$_3$ has a chiral centre. Suitable non-chiral ligands include optionally substituted aryl (e.g., optionally substituted phenyl, and napthyl) and non-chiral alkyl (e.g., butyl). Suitable chiral ligands include menthyl and fused polycyclics such as 3-cholestane and those derived from cholic acid, e.g., 3-24-norcholanyl and 7-24-norcholanyl (Schiesser et al., *Phosphorus, Sulfur, Silicon and Related Elements*, Vol 150–51, 177, 1999).

Examples of organotin hydrides include (a) (1S,2S,5R)-Menthyldiphenyltin hydride; (b) bis[(1S,2S5R)-menthyl] phenyltin hydride; and (c) 3α-dimethylstannyl-5α-cholestane, which can be prepared in accordance with the procedures described in Daktemieks et al., *Organometallics*, 3342–3347, 1999. In the following structures, "men" indicates:

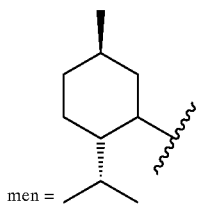

(a) menPh$_2$SnH (b) men$_2$PhSnH

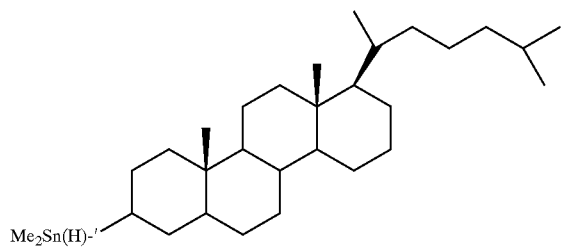

Me$_2$Sn(H)-'

(c)

Other suitable organotin hydrides include (d) and (e), shown below, which can be prepared by reaction of the appropriate aryl lithium with bis[(1S,2S,5R)-methyl] phenyltin chloride followed by LiAlH$_4$ reduction (Daktemieks et al., supra, and Jastrzebski et al, *J. Organomet. Chem.*, 1983, 246, C75 and van Koten et al, *Tetrahedron* 1989, 45, 569). Other aryl tin hydrides can be made in an analogous manner. Further examples of a suitable organotin hydride include (d) as below, where one of the menthyl groups is replaced by a phenyl group (both diasteroisomers). Other exemplary preferred compounds of the invention include, for example, (f) shown below.

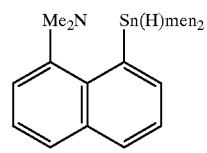

(d)

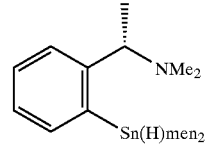

(e)

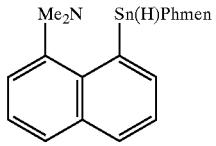

(f)

Lewis acids for use with the method of the present invention are compounds which are able to accept an electron pair, ie., co-ordinate with an electron donator. Suitable Lewis acids include transition metal complexes and compounds wherein the metal center can accept an electron pair. Examples of suitable Lewis acids include AlCl$_3$, BF$_3$, BBr$_3$, BCl$_3$, TiCl$_4$, FeCl$_3$, ZnCl$_2$, zirconocene dichloride (herein after referred to as (i)), trialkylborates (RO$_3$B, wherein each R is an alkyl group which can be the same or different), (S,S)- and (R,R)-(+)-N,N'-bis(3,5-di-tert-butylsalycidene)-1,2-diaminocyclohexamanganese (III) chloride (hereinafter referred to as (ii) and (iii) respectively) (Jacobson's catalyst, Jacobsen et al., *J. Am. Chem. Soc.*, 113:7063, 1991). An increase in the size of the Lewis acid may result in an increase in enantioselectivity. (See, for example, entries 3–5, 8–10, 13–15 and 18–20 of Table 1 in Example 1 where the addition of (ii) or (iii) provided greater ee values than the use of (i), with, in many cases, (i) providing a greater enantiomeric excess (ee) compared to BF$_3$.

The reductive methods of the invention are carried out for a time and under conditions sufficient to effect enantioselective reduction of a suitable prochiral radical precursor by hydrogen. Suitable reaction temperatures, solvents and quantities of stannane and initiator for free radical reductions are known in the art (see, for example, Perchyonok et al, *Tetrahedron. Lett.*, 39:5437, 1998 and references cited therein). Preferred solvents include hydrocarbon solvents, e.g., toluene. The reduction is preferably carried out at temperature less than 0° C., preferably less than about −30° C., more preferably at about −78° C. Exemplary initiators include those which are reactive at these temperatures such as AMBM (*Tetrahedron Lett.*, 38:6301, 1997); 9-BBN (*Tetrahedron Lett.*, 39:5437, 1998), 9-alkyl-9-BBN (e.g., alkyl=ethyl, propyl, butyl, etc.).

The stannane is preferably used in an amount of about 0.5–1.5 equivalents of substrate per reductive site, i.e., central prochiral carbon atom, more preferably about 1.1 equivalents, to effect optimum reductive conversion.

The Lewis acid is preferably used in an amount of about 0.9–1.1 equivalents of substrate, per reductive site, i.e., central prochiral carbon atom, more preferably about 1.0 equivalent. Lesser amounts can be used such as 0.1 or 0.5 equivalents although lower enantiomeric excesses (ees) are usually observed. The addition of higher amounts of Lewis acid can also be used, although this does not generally result in an increase in observed ees.

The stereochemistry of the reduced prochiral carbon center in the resulting compound can be R or S.

The methods of the invention may be particularly useful in preparing optically enhanced amino acids. Thus, α- or β-carbon centered radicals derived from α- or β-substituted amino acids may be reduced by the methods of the invention to produce optically enhanced amino acids which may be natural or unnatural, including alanine, asparagine, cysteine, glutamine, isoleucine, leucine, methionine, phenylalanine, proline, serine, threonine, tryptophan, tyrosine, valine, aspartic acid, glutamic acid, arginine, histidine, lysine and their homo derivatives. Other examples include α- and β-straight and branched chain alkyl substituted amino acids, α- and β-cycloalkyl substituted amino acids, and α- and β-aryl substituted amino acids.

The chiral stannanes for the generation of the prochiral carbon centered radical may also be immobilized onto a solid support, e.g., a polymeric support, such as pins, beads or wells, for use in the methods of the invention, e.g., used in combinatorial techniques known in the art.

The invention will now be described with reference to the following non-limiting examples which are included for the purpose of illustrating the invention only and are not to be construed as limiting the generality hereinbefore described.

EXAMPLES

Example 1

Reduction of Compounds (1a)-(1d) and (2).

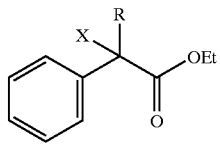

-continued

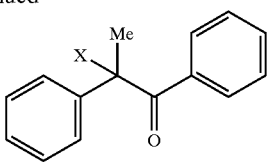

1a. R=Me, X=Br
1b. R=Et, X=Br
1c. R=cyclopentyl X=Br
1d. R=Bu$^t$, X=Br
2. X=Br

Compounds 1a–d and 2 (X=Br) were prepared according to the methods of Metzger et al, *Angew. Chem., Int., Ed. Engl.*, 36:235, 1997, and Curran et al, *Tetrahedron: Asymmetry*, 7:2417, 1996.

Reductions were carried out at concentrations of approximately 0.1 M of the substrate in to which 1.0 equiv. of the Lewis acid of choice and 1.1 equiv. of the stannane were added in toluene at −78° C., initiated using 9-BBN (Perchyonok et al, *Tetrahedron. Lett*, 39:5437, 1998). Reactions were carried out until TLC analysis indicated the absence of starting material (ca. 1–2 hr) at which time the reaction mixtures were examined by chiral-phase gas chromatography (CG) and the percentage conversion and enantiomeric ratios determined by integration of the signals corresponding to the mixture of reduced compounds 1 and 2 (X=H) against an internal standard (either octane or undecane). Reduced compounds 1 and 2 (X=H) were identified by comparison of their GC retention times with those of the authentic compounds. The absolute configuration of the dominant isomer in each case was assigned by comparison with the GC retention times of the (S)-products 1 and 2 prepared and resolved following literature procedures (Campbell et al, *J. Chem. Soc.*, 25, 1946; Aaron et al, *J. Org. Chem.*; and Elhafez et al, *J. Am. Chem. Soc.*, 74:5846, 1952). Gas chromatographic analyses of the reaction mixtures were carried out using a chiral trifluoroacteylated γ-cyclodextrin (Chiraldex™ G-TA, 30 m×0.25 mm) capillary column purchased from Alltech.

Table 1 lists enantioselectivity data for the model substrates 1 and 2 (X=Br) reacting with bis[(1S,2S,5R)-menthyl]phenyltin hydride at −78° C. in toluene in the absence of any additive and in the presence of 1 equiv. of BF$_3$, zirconocene dichloride (i), (S,S)-(−)- or (R,R)-(+)-N, N'-bis(3,5-di-tert-butylsalycidene)-1,2-diaminocyclohexanemanganese (III) chloride (ii) or (iii) respectively.

All reductions gave the (S) product. The conversion is cited as that measured by GC, with the exception of entries 9 and 14 which are isolated yields.

TABLE 1

Enantioselectives observed for reactions involving bis[(1S,2S,5R)-menthyl]phenyltin hydride (b) in toluene at −78° C.

| Entry | Substrate | Lewis Acid | Ee (%) | Conversion (%) |
|---|---|---|---|---|
| 1 | 1a | None | 2 | 80 |
| 2 | 1a | BF$_3$ | 32 | 64 |
| 3 | 1a | (i) | 36 | 58 |
| 4 | 1a | (ii) | 60 | 81 |
| 5 | 1a | (iii) | 55 | 59 |
| 6 | 1b | None | 4 | 81 |
| 7 | 1b | BF$_3$ | 20 | 68 |
| 8 | 1b | (i) | 46 | 52 |

TABLE 1-continued

Enantioselectives observed for reactions involving bis[(1S,2S,5R)-menthyl]phenyltin hydride (b) in toluene at −78° C.

| Entry | Substrate | Lewis Acid | Ee (%) | Conversion (%) |
|---|---|---|---|---|
| 9 | 1b | (ii) | 86 | 75 (71°) |
| 10 | 1b | (iii) | 84 | 69 |
| 11 | 1c | None | 9 | 81 |
| 12 | 1c | $BF_3$ | 30 | 79 |
| 13 | 1c | (i) | 35 | 74 |
| 14 | 1c | (ii) | 80 | 82 (71°) |
| 15 | 1c | (iii) | 78 | 75 |
| 16 | 1d | None | 6 | 82 |
| 17 | 1d | $BF_3$ | 10 | 76 |
| 18 | 1d | (i) | 60 | 68 |
| 19 | 1d | (ii) | 80 | 72 |
| 20 | 1d | (iii) | 83 | 52 |
| 21 | 2 | None | 16 | 81 |
| 22 | 2 | $BF_3$ | 12 | 69 |
| 23 | 2 | (i) | 52 | 92 |
| 24 | 2 | (ii) | 52 | 76 |
| 25 | 2 | (iii) | 50 | 60 |

Example 2

Table 2 lists the effect that different organotin hydrides have on the observed enantioselectivities at −78° C. for reactions involving Lewis acids, (i), (ii) and (for one example) (iii) Reactions were carried out in accordance with the procedure described in Example 1. It should be noted that the achiral stannane, tributyltin hydride, reacts with 1d (X=Br) in the presence of Lewis acids (i) and (ii) to afford 1d (X=H) with 0 and 8% ee, respectively.

TABLE 2

Enantioselectivites observed for reactions involving zirconocene dichloride (i) and (S,S)-(-)-N,N'-bis(3,5-di-tert-butylsalycidene)-1,2-di-aminocyclohexanemanganese (III) chloride (ii) and its enantiomer (iii) in toluene at −78° C.

| Entry | Substrate | Lewis Acid | Stannane | Ee (%) | Yield (%) |
|---|---|---|---|---|---|
| 1 | 1a | (i) | (a) | 36(S) | 59 |
| 2 | 1a | (i) | (d) | 38(S) | 77 |
| 3 | 1a | (i) | (c) | 60(S) | 82 |
| 4 | 1a | (ii) | (a) | 60(S) | 82 |
| 5 | 1a | (ii) | (e) | 90(S) | 73 (68) |
| 6 | 1a | (ii) | (c) | 34(S) | 58 |
| 7 | 1b | (i) | (a) | 42(S) | 51 |
| 8 | 1b | (i) | (d) | 52(S) | 79 |
| 9 | 1b | (i) | (c) | 54(S) | 54 |
| 10 | 1b | (ii) | (b) | 70(S) | 78 |
| 11 | 1b | (ii) | (e) | 72(S) | 68 |
| 12 | 1b | (ii) | (c) | 62(S) | 67 |
| 13 | 1b | (iii) | ent-(b) | 86(R) | 72 |
| 14 | 1c | (ii) | (e) | 96(S) | 75 (67) |
| 15 | 1d | (i) | $Bu_3SnH$ | 0(—) | — |
| 16 | 1d | (i) | (a) | 58(S) | 63 |
| 17 | 1d | (i) | (d) | 62(S) | 87 |
| 18 | 1d | (i) | (c) | 76(S) | 96 |
| 19 | 1d | (ii) | $Bu_3SnH$ | 8(S) | — |
| 20 | 1d | (ii) | (a) | 72(S) | 74 |
| 21 | 1d | (ii) | (e) | 80(S) | 76 |
| 22 | 1d | (ii) | (c) | 82(S) | 72 (68) |
| 23 | 2 | (i) | (a) | 50(S) | 68 |
| 24 | 2 | (i) | (d) | 56(S) | 62 |
| 25 | 2 | (i) | (c) | 42(S) | 79 |
| 26 | 2 | (ii) | (a) | 58(S) | 81 |
| 27 | 2 | (ii) | (d) | 46(S) | 85 |
| 28 | 2 | (ii) | (e) | 62(S) | 74 |
| 29 | 2 | (ii) | (c) | 52(S) | 72 | those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

What is claimed:

1. A method for enantioselectively reducing a prochiral carbon centred radical having one or more electron donator groups attached directly to the central prochiral carbon atom of the radical, and/or attached to a carbon atom within 1 to 4 atoms of the central prochiral carbon atom, comprising treating said radical with a chiral non-racemic organotin hydride in the presence of a Lewis acid.

2. The method of claim 1, wherein the electron donator group is attached directly to the central prochiral carbon atom or to a carbon atom within 1 or 2 atoms of the central prochiral carbon atom.

3. The method of claim 1, wherein the prochiral carbon centred radical is a prochiral amino acid carbon centred radical wherein the central prochiral carbon atom is an α-carbon atom of an α-amino acid or a β-carbon atom of a β-amino acid.

4. The method of claim 1, wherein the prochiral carbon centred radical is generated from a radical precursor selected from the group consisting of: aryl selenides, aryl sulphides, aryl tellurides, xanthates, thionoformates, Barton esters and tertiary chiral halosubstrates.

5. The method of claim 1, wherein the electron donator group is a carbonyl group.

6. The method of claim 1, wherein the organotin hydride is selected from the group consisting of:

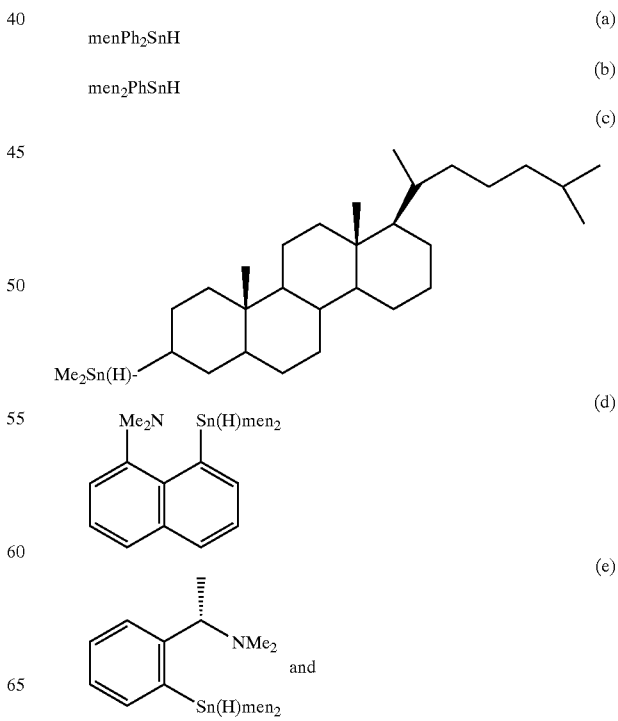

-continued

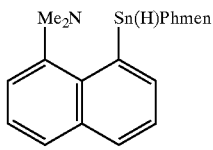
f)

7. The method of claim 1, wherein the Lewis acid is selected from the group consisting of: $AlCl_3$, $BF_3$, $BBr_3$, $BCl_3$, $TiCl_4$, $FeCl_3$, $ZnCl_2$, zirconocene dichloride, trialkylborates and (S,S)- and (R,R)-(+)-N,N'-bis(3,5-di-tert-butylsalycidene)-1,2-diaminocyclohexamanganese (III) chloride.

8. The method of claim 1, wherein the Lewis acid is used in an amount of about 0.9 to about 1.1 equivalents per prochiral carbon centred radical to be reduced.

9. The method of claim 1, wherein the organotin hydride is used in an amount of about 0.5 to about 1.5 equivalents of substrate per prochiral carbon centred radical to be reduced.

10. The method of claim 1, wherein the organotin hydride is immobilized onto a solid support.

* * * * *